United States Patent [19]
Tsukamoto et al.

[11] Patent Number: 5,666,395
[45] Date of Patent: Sep. 9, 1997

[54] X-RAY DIAGNOSTIC APPARATUS

[75] Inventors: Akira Tsukamoto; Masayuki Nishiki; Koichiro Nabuchi, all of Otawara; Shin-ichi Yamada, Kawachi-gun; Tohru Saisu, Otawara; Takayuki Tomisaki; Manabu Tanaka, both of Yokohama; Seiichiro Nagai, Otawara, all of Japan

[73] Assignee: Kabushiki Kaisha Toshiba, Kawasaki, Japan

[21] Appl. No.: 715,086

[22] Filed: Sep. 17, 1996

[30] Foreign Application Priority Data

Sep. 18, 1995 [JP] Japan ................................ 7-238322

[51] Int. Cl.$^6$ ........................................... G21K 1/00
[52] U.S. Cl. ...................... 378/98.4; 378/154; 378/149; 250/370.09; 250/580
[58] Field of Search ..................... 378/19, 145, 98.4, 378/147, 149, 154, 98.8; 250/370.09, 370.11, 580

[56] References Cited

U.S. PATENT DOCUMENTS

| | | | |
|---|---|---|---|
| 4,672,207 | 6/1987 | Derenzo | 250/370.11 |
| 4,689,487 | 8/1987 | Nishiki et al. | 250/361 R |
| 4,785,186 | 11/1988 | Street et al. | 250/370.14 |
| 5,179,284 | 1/1993 | Kingsley et al. | 250/370.11 |
| 5,436,958 | 7/1995 | Taylor | 378/147 |
| 5,557,650 | 9/1996 | Guida et al. | 378/154 |
| 5,596,198 | 1/1997 | Perez-Mendez | 250/370.11 |

*Primary Examiner*—Don Wong
*Attorney, Agent, or Firm*—Oblon, Spivak, McClelland, Maier & Neustadt, P.C.

[57] ABSTRACT

It is an object of the invention to provide an X-ray diagnosis apparatus having an X-ray plane detector capable of removing the influence of a scattered X-ray by using a grid and also preventing a Moiré image. An X-ray image transmitted through a target object is sensed by a plane detector in units of pixels which are two-dimensionally arranged at a predetermined pitch. A scattered X-ray incident on the plane detector is removed by a scattered ray removing grid having plate-like X-ray shielding members and arranged on an X-ray incident side of the plane detector. The X-ray shielding members are arranged such that an X-ray shielding pattern on the X-ray incident surface of the plane detector has a pitch corresponding to an integer fraction of the arrangement pitch of the pixels. When a steady positional relationship is kept between the pitch of the X-ray detection elements and the period of the fringe pattern of the X-ray which is shielded by the grid, a Moiré image can be prevented.

8 Claims, 5 Drawing Sheets

X-RAY DIAGNOSTIC APPARATUS

BACKGROUND OF THE INVENTION

1. Field of the Invention

The present invention relates to an x-ray diagnosis apparatus having an X-ray plane detector.

2. Description of the Related Art

An X-ray diagnosis apparatus irradiates an X-ray on a target object and detects the X-ray transmitted through the target object, thereby obtaining the X-ray diagnosis image of the target object. As an X-ray detection system used for such an X-ray diagnosis apparatus, there is provided a screen film system, a computed radiography (CR) system using an imaging plate, an image intensifier-TV (II-TV) system using an image intensifier and a TV unit, or the like is used.

In recent years, an X-ray plane detector serving as an X-ray detection system has received a great deal of attention because it has plural advantages, i.e., the portability of the screen film system or CR system, the high resolution of the screen film system, and the real-time properties of the II-TV system.

The X-ray plane detector comprises, for example, a phosphor for converting an X-ray into a light, a photodiode for converting the light into electric charges, a capacitor for accumulating the electric charges, and a TFT (Thin Film Transistor) serving as a switching gate for reading out the charges. One detection element comprises one photodiode, one capacitor, and one TFT. The X-ray plane detector is constituted by two-dimensionally arranging a plurality of such detection elements in accordance with the number of pixels.

In the conventional X-ray photography, a scattered X-ray removing grid is used to remove scattered X-ray components generated upon X-ray irradiation and acting on the photographed image. When a photographing operation is performed by an X-ray diagnosis apparatus to which the above-described conventional plane detector is applied, a Moiré image, i.e., a kind of fixed pattern noise is generated in the photographed image.

Figure 1:
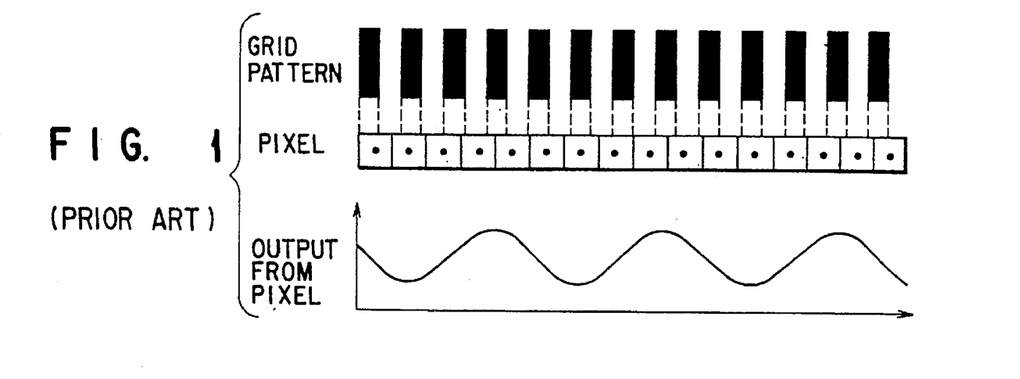
FIG. 1 is a view schematically showing the positional relationship between the pixels and the grid pattern of the conventional X-ray plane detector, and the state of outputs from the respective pixels, which is observed when an X-ray is uniformly irradiated.

As shown in FIG. 1, when the relationship between the pitch of image sensing pixels (e.g., a line of pixels along the data signal line), the pixels being represented by a square frame: a black dot represents the central portion of a pixel, and the period of the grid pattern, which generates a Moiré, does not keep a steady positional relationship between the pixels and the fringe pattern, the waving phenomenon of amplitude variations having a long period (Moiré phenomenon) is generated. Such a Moiré image, i.e., noise must be removed from the image.

SUMMARY OF THE INVENTION

Accordingly, it is an object of the present invention to provide an X-ray diagnosis apparatus having an X-ray plane detector capable of removing the influence of a scattered X-ray by using a grid and also preventing a Moiré image.

According to the present invention, there is provided an X-ray diagnosis apparatus comprising:

means for irradiating an X-ray on a target object;

means, having pixels which are two-dimensionally arranged at a predetermined pitch, for sensing an X-ray image transmitted through the target object; and a scattered X-ray shielding grid which has X-ray shielding members which are arranged at a pitch corresponding to an integer fraction of the arrangement the pitch of the pixels.

According to the X-ray diagnosis apparatus of the present invention, when a steady positional relationship is kept between the pitch of the X-ray detection elements and the period of the fringe pattern of the X-ray which is shielded by the grid, a Moiré image can be prevented.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which.

DETAILED DESCRIPTION OF THE PREFERRED EMBODIMENTS

Figure 2:
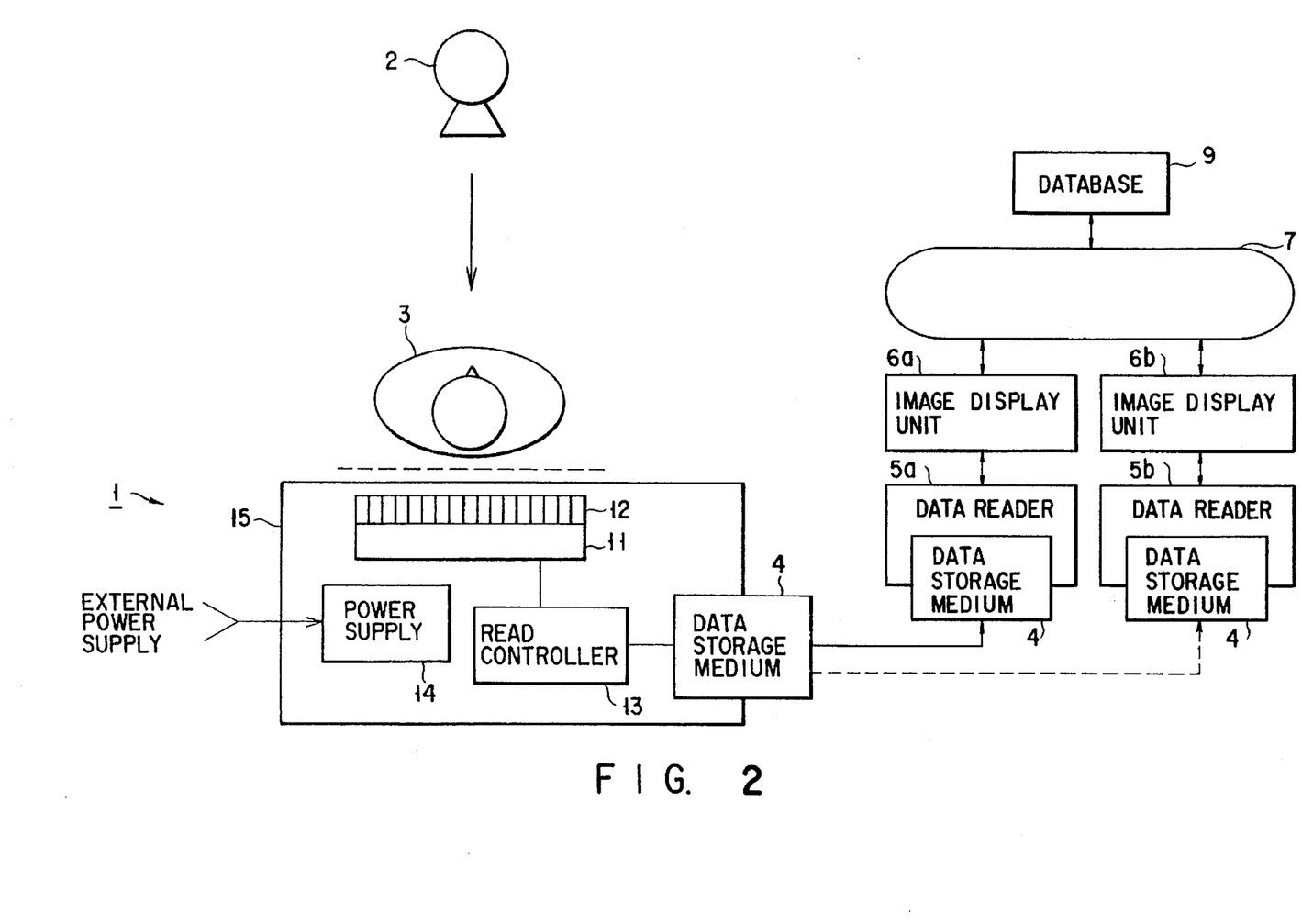
FIG. 2 is a block diagram showing the overall arrangement of an X-ray image sensing system according to the first embodiment of the present invention.

An X-ray apparatus according to an embodiment of the present invention will be described below with reference to the accompanying drawings. FIG. 2 is a block diagram showing the overall arrangement of an X-ray image sensing system to which the present invention is applied.

Reference numeral 1 denotes an X-ray image detection cassette using an X-ray plane detector. An X-ray irradiation unit 2 generates an X-ray and irradiates the X-ray on a target object on a bed at a desired dose. The X-ray transmitted through a target object 3 is detected by the X-ray image detection cassette 1.

The X-ray image detection cassette 1 comprises an X-ray plane detector 11 for sensing an X-ray image, a grid 12, a data storage medium 4 (e.g., a semiconductor memory or a compact hard disk) detachably attached to store the X-ray image sensed by the X-ray plane detector 11, a read controller 13 for reading out data from the X-ray plane detector 11 and storing the data in the data storage medium 4, a power supply 14 for supplying power, and a housing 15 which integrally contains these constituent elements. The power supply 14 has a battery and a charger for charging the battery with external power supplied through an AC outlet or the like. The housing 15 comprises a case having a portable cassette-like shape or a stationary cassette-like shape.

Figure 3:
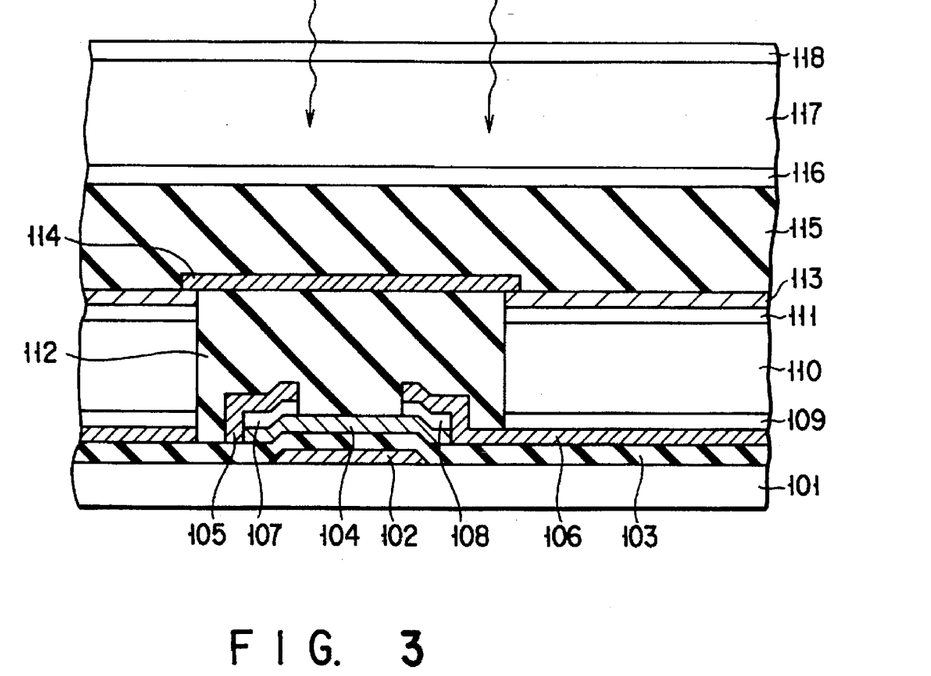
FIG. 3 is a sectional view showing the structure of an actual X-ray detection element constituting an X-ray plane detector.

FIG. 3 is a sectional view showing the arrangement of an X-ray plane detector 11 using TFT-photodiodes.

A TFT is formed in the following manner. A gate electrode 102 is formed in each of a plurality of TFT regions on a support 101, and an SiNx layer 103 is formed on the resultant structure. An aySi layer 104, a drain electrode 105, and a source electrode 106 are formed on the SiNx layer 103. The drain electrode 105 and the source electrode 106 are connected to each other through the aySi layer 104 such that the two electrodes are not in direct contact with each other. N+ aySi layers 107 and 108 are formed in gaps between the drain electrode 105 and the aySi layer 104 and between the source electrode 106 and the aySi layer 104, respectively.

A photodiode is formed in the following manner. An n+ layer 109, an i layer 110, and a p+ layer 111 are formed on the SiNx layer 103 and the source electrode 106, which are formed on the support 101, so that a photodiode with a Pin structure is formed.

A first polyimide layer 112 is formed on the TFT. A transparent electrode 113 is formed on the photodiode. A metal electrode 114 is formed on the first polyimide layer 112 to connect the transparent electrodes 113 on adjacent regions.

A second polyimide layer 115 is formed on the transparent electrode 113 and the metal electrode 114. A transparent protective layer 116, a phosphor 117, and a light-reflecting layer 118 are formed on the second polyimide layer 115.

Figure 4:
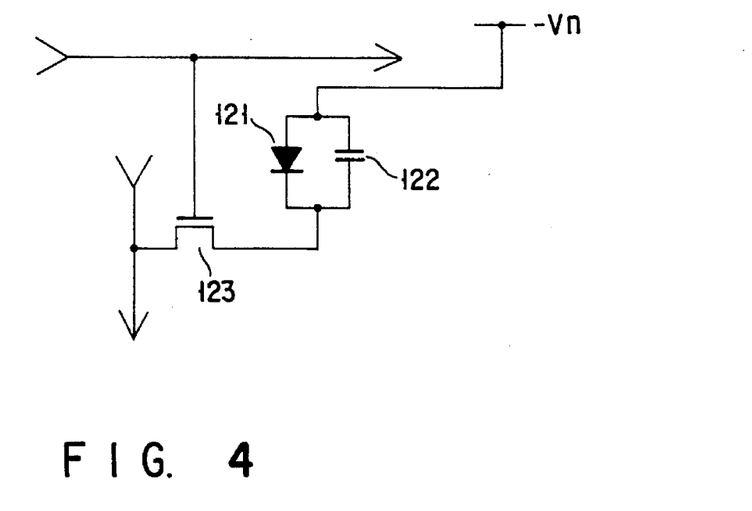
FIG. 4 is a circuit diagram showing the X-ray detection element constituting the X-ray plane detector.

As shown in FIG. 4, a photodiode 121 and a TFT 123 are electrically connected to each other. The photodiode 121 is parallelly connected to a capacitor (to be referred to as an accumulating capacitor hereinafter) 122. The cathode terminal of the photodiode 121 and one terminal of the accumulating capacitor 122 are connected to a reverse power supply (−Vn). The anode terminal of the photodiode 121 and the other terminal of the accumulating capacitor 122 are connected to the source terminal (source electrode 106) of the TFT 123. As will be described later, the gate terminal of the TFT 123 is connected to a gate driving line, and the drain terminal of the TFT 123 is connected to a data signal line.

Figure 5:
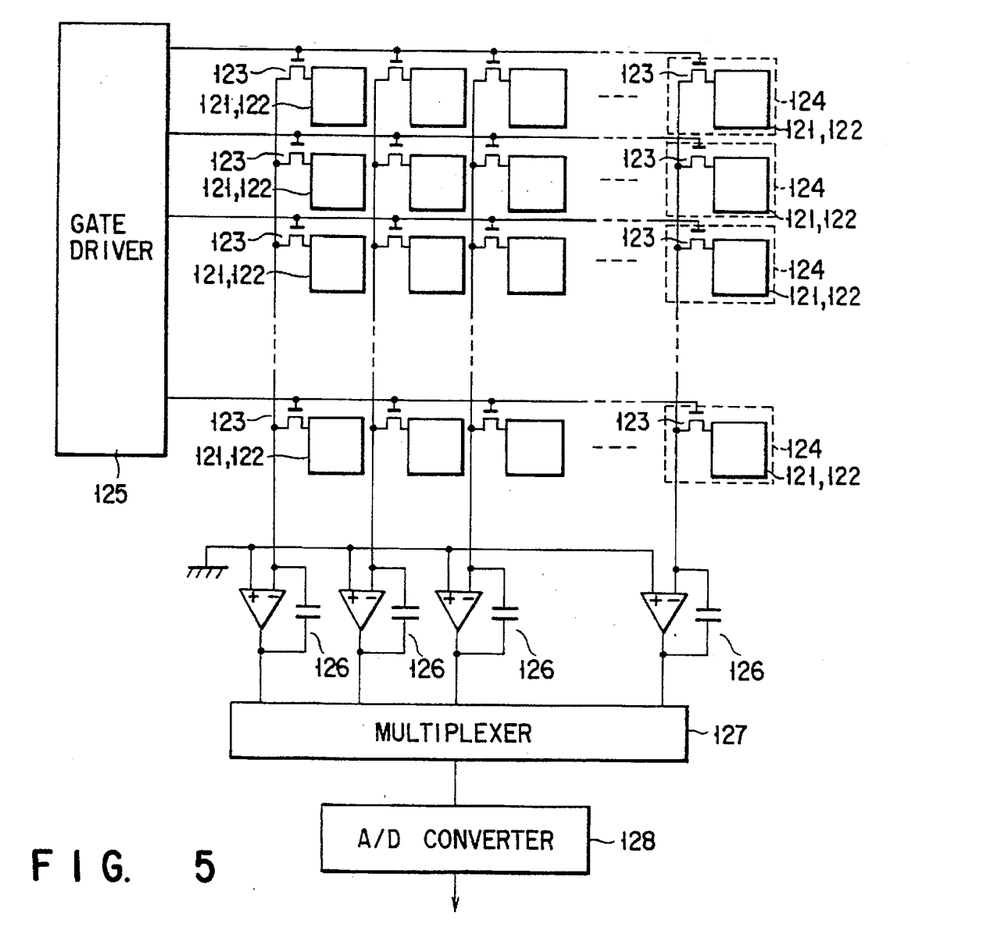
FIG. 5 is a circuit diagram showing the arrangement of the X-ray plane detector.

FIG. 5 is a circuit diagram showing the arrangement of the X-ray plane detector 11.

In the X-ray plane detector 11, a plurality of X-ray detection elements 124 each consisting of the photodiode 121, the capacitor 122, and the TFT 123 are arranged in the column and line directions.

The gate terminals of the TFTs 123 are commonly connected as gate driving lines in units of lines and connected to the line output terminals of a gate driver 125. The drain terminals of the TFTs 123 are commonly connected as data signal lines in units of columns. The drain terminals are Connected to the input terminals of a multiplexer 127 through integrating circuits 126. Each integrating circuit 126 comprises a read-out amplifier, a capacitor (to be referred to as a time-constant capacitor hereinafter), and a reset switch (not shown).

Pulse-like control signals are time-serially output from the line output terminals of the gate driver 125 in units of lines. In accordance with these pulse-like control signals, the TFTs 123 of one line are simultaneously turned on, and the TFTs 123 of another line are turned on at another time. Every time a pulse is output from each line output terminal of the gate driver 125, the multiplexer 127 time-serially receives the signal input to each input terminal one by one and outputs the signal. The output signal is input to an A/D (Analog/Digital) converter 128. The A/D converter 128 converts an analog signal into a digital signal (digital data) and outputs the digital signal.

The TFTs 123 of one line are simultaneously turned on by the pulse-like control signal output from each line output terminal of the gate driver 125. At this time, charges accumulated in the accumulating capacitor 122 are output through the TFTs 123, and this current is converted into a voltage through the integrating circuits 126.

A detection signal from each X-ray detection element 124, which is sequentially output from the multiplexer 127 one by one (in units of pixels of one line), is sequentially read in units of pixels. When one line is completely read, read access of the next line is started. Like the scanning lines of a TV unit, the detection signal is read in units of lines, so that detection data for one frame is output.

In the X-ray plane detector 11 having the above arrangement, the X-ray transmitted through a target object from the upper side is incident on the phosphor 117 through the light-reflecting layer 118. In this case, the visible light incident from the upper side is reflected by the light-reflecting layer 118 such that the visible light is not incident on the phosphor 117.

The energy of the incident X-ray is converted into an optical energy (visible light) by the phosphor 117. This visible light is transmitted through the transparent protective layers 116 and the second polyimide layer 115 and received by the photodiode 121 (the n+ layer 109, the i layer 110, and the p+ layer 111) having a sensitivity to visible light through the transparent electrode 113.

The light is converted by the photodiode 121 into charges proportional to the light intensity. The charges are accumulated in the accumulating capacitor 122. The accumulated charges are read out by the TFTs 123 in units of pixels for each line (in units of columns) through the data signal line, as described above. The readout signal is proportional to the intensity of the X-ray. When signals read out in units of pixels are reconstructed, the X-ray image can be sensed.

Consequently, the X-ray image sensed by the X-ray plane detector 11 is stored in the storage medium 4. When the data storage medium 4 is detached from the X-ray image detection cassette 1 and attached to a data reader 5a/5b (to be described later), image data can be transferred.

The data reader 5a/5b reads image data from the attached data storage medium 4 and stores the data in an internal memory, and at the same time, outputs the data to an image display unit 6a/6b. The image display unit 6a/6b reconstructs the image data into an image and displays the image on the screen of a display unit.

This image display unit 6a and 6b are connected to a communication line (e.g., a LAN: Local Area Network) 7. Image display units 6a and 6b, and databases 9, which are located at various places, are connected to the communication line 7.

An X-ray image data read by the data reader 5a/5b connected to one of image display unit 6a/6b is transmitted by the image display unit 6a/6b through the communication line 7 and stored in the database 9. The X-ray image data stored in the database 9 can be read out by another image display unit 6a/6b through the communication line 7 and displayed on the screen of the display device of the image display unit 6a/6b.

For example, image display unit 6a connected to data reader 5a is placed in a bedroom and image display unit 6b connected to data reader 5b is placed in a doctor room (e.g., a consulting room). All the units are connected through the communication line 7.

In such a system, the X-ray image detection cassette 1 and the X-ray irradiation unit 2 are brought into the bedroom, and an X-ray image sensing operation is performed. An X-ray image obtained upon this X-ray image sensing operation is stored in the data storage medium 4 set in the X-ray image detection cassette 1. The data storage medium 4 is detached from the X-ray image detection cassette 1 and set in the data reader 5a placed in the bedroom. The X-ray image data stored in the data storage medium 4 is read out by the data reader 5a. The readout X-ray image data is transferred to the database 9 by the image display unit 6a through the communication line 7 and stored in the database 9.

The doctor sends a transfer request for the X-ray image of a desired patient from the database 9 by the image display unit 6b through the communication line 7. The X-ray image data of the desired patient is read out from the database 9 and transferred to the image display unit 6b in the consulting room of the doctor. Therefore, the X-ray image of the desired patient is displayed by the image display unit 6b, so that the doctor can perform diagnosis in the consulting room.

In the bedroom, a sensed X-ray image can be displayed in real time.

Figure 6:
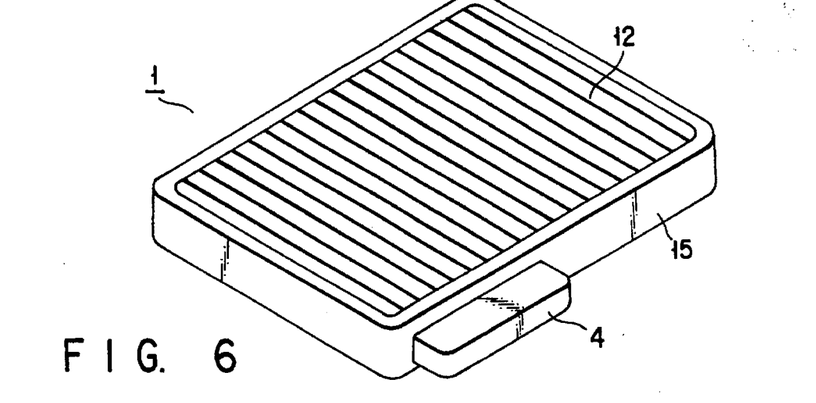
FIG. 6 is a perspective view showing an X-ray image detection cassette which contains the X-ray plane detector of the X-ray image sensing system according to the first embodiment.

FIG. 6 is a perspective view of the X-ray image detection cassette 1.

The housing 15 is constituted by a box having an opening portion on the upper surface. The opening portion of the housing 15 is closed by the fixed grid 12.

The grid 12 is used to remove the influence of scattered X-ray components and constituted by alternately bonding plate-like X-ray shielding members and plate- or rod-like X-ray transmitting members. Generally, lead is used for the X-ray shielding members, and aluminum or wood is used for the X-ray transmitting members.

The X-ray plane detector 11 and the peripheral circuits of the X-ray plane detector 11 (not shown) are contained in the box consisting of the housing 15 and the grid 12. The data storage medium 4 can be detachably connected to the peripheral circuits of the X-ray plane detector 11 through an opening portion formed on a side surface of the housing 15.

Figure 7:
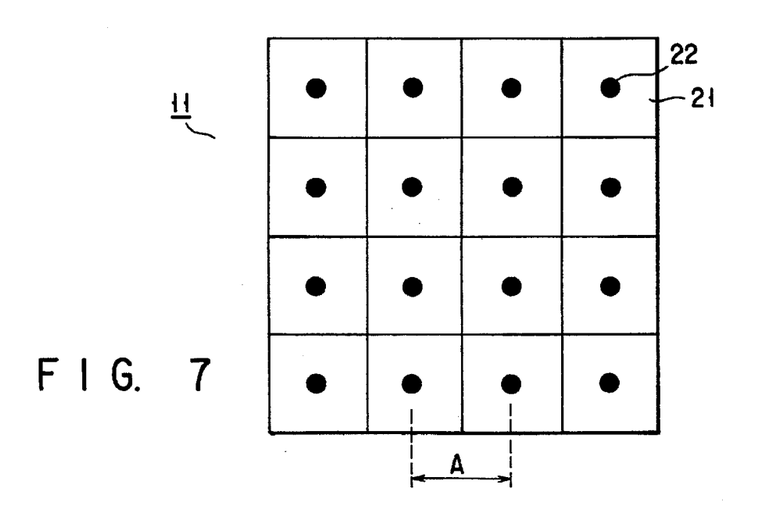
FIG. 7 is a view schematically showing the arrangement of part of the X-ray plane detector of the X-ray image sensing system according to the first embodiment.

FIG. 7 is a view schematically showing the arrangement of part of the X-ray plane detector 11.

A small square frame represents a pixel 21, i.e., an X-ray detection element 124 (formed of a phosphor 117 of FIG. 3, a photodiode 121, an accumulating capacitor 122, and a TFT 123). A black dot represents a center 22 of the X-ray sensitive portion of the pixel.

When the pitch (to be referred to as a pixel pitch hereinafter) between the centers of the pixels 21 of the X-ray plane detector 11 is A mm, the grid frequency (the number of pairs of the X-ray shielding member and the X-ray transmitting member per cm) of the grid 12 is designed as 1/A or N/A (N is an integer). That is, the pitch between the lead portions of the grid 12 is designed to equal the pixel pitch A or be an integer fraction (1/N) of the pixel pitch A.

First, description will be given with respect to the case of 1/A.

For example, the X-ray plane detector 11 has a size of, e.g., 250 mm (vertical)×300 mm (horizontal) and 2000 pixels in the vertical direction, and a pixel pitch of A=0.125 mm, and the grid frequency is 1/A=8 [1/cm].

Figure 8:
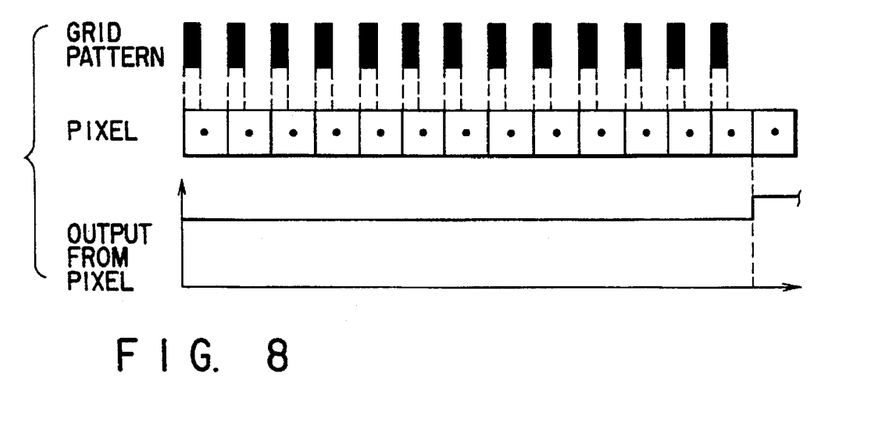
FIG. 8 is a view showing the positional relationship between the pixels and the grid pattern of the X-ray plane detector of the X-ray image sensing system of the first embodiment, and the state of outputs from the respective pixels, which is observed when an X-ray is uniformly irradiated.

FIG. 8 if a view showing the positional relationship between grid pattern of grid 12 and the pixels 21 of one line of the X-ray plane detector 11, and the state of outputs from the respective pixels 21, which is observed when an X-ray is uniformly irradiated.

In FIG.8, for the descriptive convenience, the X-ray shielding members (lead portions) of the grid pattern are exaggerated, and only one line of pixels (e.g., one line of pixels along the data signal line) is represented by the small square frame. The actual ratio of the thickness of the lead portion to that of an intermediate substance portion (X-ray transmitting member) is different. In addition, the boundaries between the pixels match the left ends of the lead portions of the grid.

In the first embodiment having the above arrangement, an X-ray is uniformly irradiated. The respective outputs from the pixels 21 are at the same level; therefore no waving such as a Moiré pattern (Moiré a image) is observed, unlike a case wherein no grid is arranged on the X-ray incident surface (front surface) of the pixels 21, though the output level from each pixel 21 is slightly decreased.

The reason why the output from each pixel 21 is decreased is that the lead portions of the grid for shielding the scattered X-ray component also shield the X-ray component which should be detected (a non-scattered X-ray component which is transmitted through the target object).

Even when the positional relationship between the pixels of the detector and the lead portion of grid is shifted, the same positional relationship is established between each lead portion and a corresponding pixel as far as the grid frequency is 1/A. Outputs from all the pixels have the same value, though the degree of decrease in output changes, so no waving such as a Moiré pattern (Moiré image) is observed.

Next, description will be given with respect to the case of N/A (N is an integer). The grid frequency is an integer multiple of 1/A [1/cm], i.e., two or more lead portions are arranged for one pixel. For example, pixel pitch of the pixels 21 is A=0.125 mm, grid frequencies are 40, 48, or 56 [1/cm] (N=5,6,7) which can be achieved in the conventional II-TV system.

These various grid frequencies are available in accordance with the clinical purpose and the type of apparatus.

In this case, the effect of removing the influence of the scattered X-ray component increases, though outputs from the pixels largely decrease.

As described above, according to the first embodiment, the grid 12 having the grid frequency 1/A or N/A (A is the pixel pitch of the X-ray plane detector) is used. With this arrangement, each lead portion of the grid 12 has the same positional relationship with respect to the corresponding pixel. When an X-ray is uniformly irradiated, outputs from all the pixels have the same value, so the influence of the scattered X-ray component can be removed. At the same time, a Moiré image is prevented, so that a satisfactory and proper X-ray image can be stably obtained.

The second embodiment of the present invention will be described below with reference to FIGS. 9 and 10. The first embodiment relates to an X-ray plane detector having no dead portions. Although, the second embodiment relates to an X-ray plane detector having dead portions, the arrangement of the lead portions of a grid is specified. The arrangement of an X-ray image sensing system is the same as that of the above-described first embodiment, and a detailed description thereof will be omitted (FIGS. 2 to 6).

Figure 9:
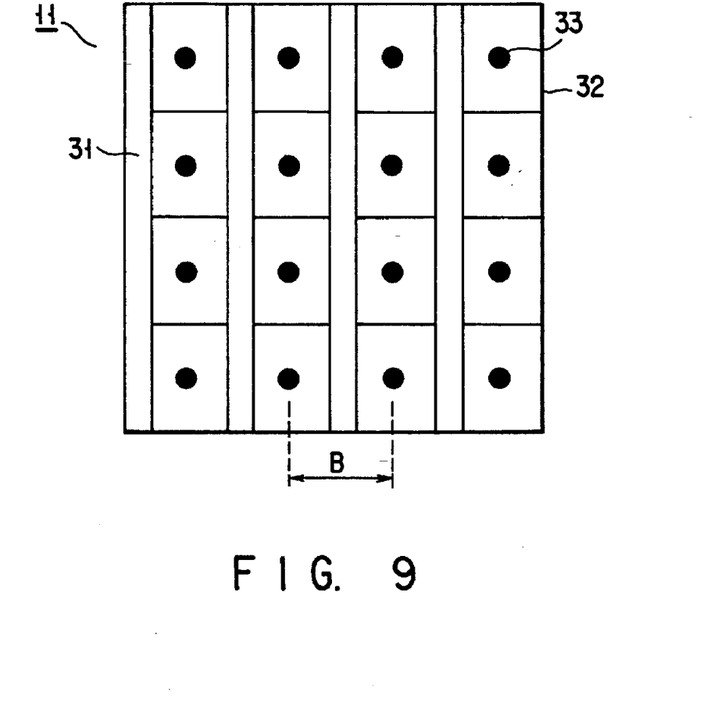
FIG. 9 is a view schematically showing the arrangement of part of an X-ray plane detector according to the second embodiment of the present invention.

FIG. 9 is a view schematically showing the arrangement of part of an X-ray plane detector 11. In this X-ray plane detector 11, dead portions (portions at which light cannot be detected) 31 are arranged in the line direction (along the gate driving line) between the lines of pixels (X-ray detection elements) 32 each represented by a small square frame. The dead portions 31 are formed because of the structure of the X-ray plane detector 11. A black dot represents a center 33 of the X-ray sensitive portion of the pixel. The pitch between the pixels 32 is B.

Figure 10:
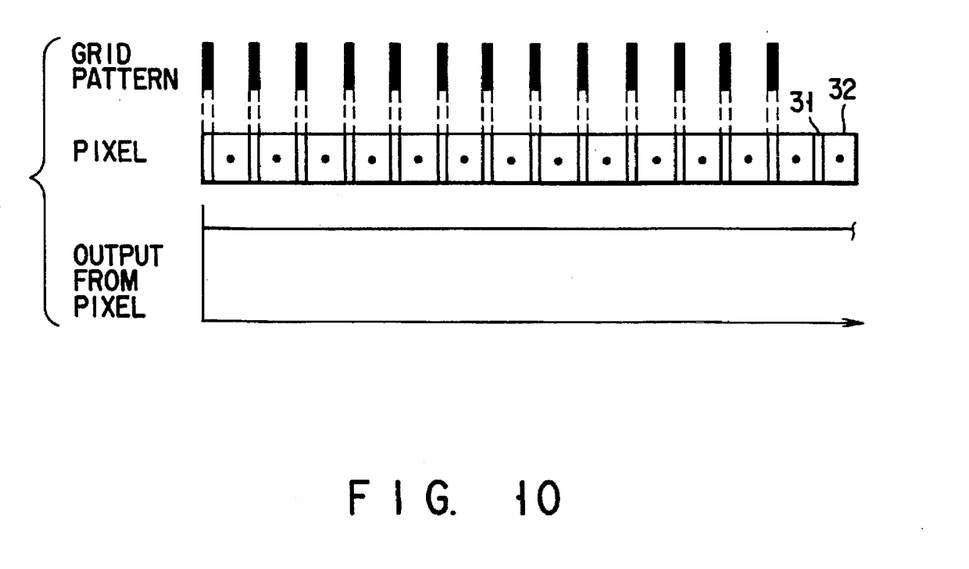
FIG. 10 is a view showing the positional relationship between the pixels and the grid pattern of the X-ray plane detector of the second embodiment, and the state of outputs from the respective pixels, which is observed when an X-ray is uniformly irradiated.

FIG. 10 is a view showing the positional relationship between the pixels 32 (pixels of one line) of the above-described X-ray plane detector 11 and the grid (GRID) pattern, and the state of outputs from the respective pixels 32, which is observed when an X-ray is uniformly irradiated.

In FIG. 10, for the descriptive convenience, the lead portions of the grid pattern are exaggerated (the actual ratio of the thickness of a lead portion to that of an intermediate substance portion is different), and only one line of pixels (e.g., one line of pixels along the data signal line) is represented by the smallest rectangular frame.

When the pitch (to be referred to as a pixel pitch hereinafter) between the centers of the pixels 32 of the X-ray plane detector 11 is B mm, the grid frequency of a grid 12 is designed as 1/B or N/B (N is an integer). That is, the pitch between the lead portions of the grid 12 is designed to equal the pixel pitch B or be an integer fraction of the pixel pitch B.

In this case, the grid frequency is designed to be 1/B. The pitch between the lead portions of the grid 12 is B. In addition, the grid 12 is fixed to the housing 15 of the cassette 1 such that the lead portions are arranged to match the dead portions 31 of the X-ray plane detector 11.

In the second embodiment having the above arrangement, an X-ray is uniformly irradiated. As for outputs from the respective pixels 32, no waving such as a Moiré a pattern (Moire image) is observed, and an output from any pixel 32 is not decreased, as shown in FIG. 10.

As described above, according to the second embodiment, the same effects as in the first embodiment can be obtained. Since the grid 12 is fixed to the housing 15 of the X-ray image cassette 1 such that the lead portions are arranged to match the dead portions 31 of the X-ray plane detector 11, an X-ray image can be sensed without decreasing output from the pixels 32.

In FIG. 10, the width of the lead portion of the grid 12 almost equals that of the dead portion 31. However, the width of the lead portion does not always need equal that of the dead portion 31 and may be smaller or larger than that of the dead portion 31. When the width of the lead portion is larger than that of the dead portion, outputs from the pixels 32 decrease, though the decrease can be minimized.

Even when the grid frequency is an integer multiple of 1/B, outputs from the pixels 32 decrease because at least one lead portion is arranged on the X-ray incident surface of the pixel 32, as a matter of course. However, this decrease can also be minimized, so that waving such as a Moiré pattern (Moiré image) can be prevented.

According to present invention, an X-ray diagnosis apparatus having an X-ray plane detector capable of removing the influence of a scattered X-ray by using a grid and also preventing a Moiré image is provided.

In the above embodiments, an X-ray is detected by a phosphor, a photodiode, an accumulating capacitor, and a TFT. However, an element for directly converting an X-ray into an electrical signal may be used in place of the phosphor and the photodiode.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray diagnosis apparatus comprising:
   means for irradiating an X-ray on a target object;
   means, having pixels which are two-dimensionally arranged at a predetermined pitch, for sensing an X-ray image transmitted through said target object; and
   a scattered X-ray shielding grid which has X-ray shielding members which are arranged at a pitch corresponding to an integer fraction of the predetermined pitch of said pixels.

2. An apparatus according to claim 1, wherein the pitch of said X-ray shielding members equals the arrangement pitch of said pixels.

3. An apparatus according to claim 1, further comprising a portable cassette-like case to cover said sensing means and said grid.

4. An apparatus according to claim 1, further comprising a stationary cassette-like case to cover said sensing means and said grid.

5. An apparatus according to claim 1, wherein said sensing means comprises:
   a fluorescent plate for converting the X-ray image into an optical image; and
   a plurality of photodetection elements for converting the optical image from said fluorescent plate into an image signal, the elements corresponding to said pixels.

6. An apparatus according to claim 1, wherein said sensing means comprises a plurality of X-ray image detection elements for converting the X-ray into an image signal, the elements corresponding to said pixels.

7. An X-ray diagnosis apparatus comprising:
   means for irradiating an X-ray on a target object;
   means, having pixels which are two-dimensionally arranged at a predetermined pitch, for sensing an X-ray image transmitted through said target object; and
   a scattered X-ray shielding grid which has X-ray shielding members which are arranged at a pitch corresponding to an integer fraction of the predetermined pitch of said pixels,
   wherein said X-ray shielding members overlap an X-ray dead portion of said sensing means.

8. A X-ray diagnosis method using an X-ray plane detector, comprising the following steps of:

irradiating an X-ray from an X-ray tube on a target object; and sensing an X-ray image transmitted through said target object by using a plane detector having pixels which are two-dimensionally arranged at a predetermined pitch and having a scattered X-ray shielding grid including X-ray shielding members having a pitch corresponding to an integer fraction of arrangement said pitch of said pixels.

* * * * *